United States Patent [19]

Patterson et al.

[11] Patent Number: 5,295,831
[45] Date of Patent: Mar. 22, 1994

[54] DISPOSABLE TORQUE WRENCH FOR DENTAL COMPONENTS

[75] Inventors: Chad J. Patterson, Plantation; Richard A. Smolowitz; Bruce L. Nickerson, both of Davie, all of Fla.

[73] Assignee: Impla-Med, Inc., Sunrise, Fla.

[21] Appl. No.: 946,924

[22] Filed: Sep. 17, 1992

[51] Int. Cl.⁵ .................... A61C 3/00; A61C 8/00; B25B 23/153
[52] U.S. Cl. ................... 433/141; 81/471; 433/173
[58] Field of Search .......... 433/141, 163, 173, 174; 81/436, 467, 471

[56] References Cited

U.S. PATENT DOCUMENTS

| | | | |
|---|---|---|---|
| 2,518,886 | 8/1950 | Halvorsen | 81/436 |
| 3,331,267 | 7/1967 | Tietge | 81/471 |
| 3,753,625 | 8/1973 | Fabrizio et al. | 81/471 X |
| 3,888,144 | 6/1975 | Parsons | 81/436 |
| 3,935,761 | 2/1976 | Junkel et al. | 433/126 X |
| 4,480,997 | 11/1984 | Deutsch et al. | 433/221 |
| 4,838,134 | 6/1989 | Ruland | 81/467 |
| 5,105,690 | 4/1992 | Lazzara et al. | 81/436 |

FOREIGN PATENT DOCUMENTS 2486852  1/1982  France ................. 81/471

Primary Examiner—John J. Wilson
Assistant Examiner—Nicholas D. Lucchesi
Attorney, Agent, or Firm—David P. Gordon

[57] ABSTRACT

A torque wrench particularly suited for applying a selected maximum torque to a dental implant component is constructed of a single shaft of predetermined material and dimension with an undercut or relieved portion therein such that application of a predetermined torque to the dental component through the shaft produces a deformity in the shaft at the relief. The shaft is designed with one end to engage the implant component or device coupled thereto. Where the shaft is straight, the other end of the shaft is designed to engage a driver. Alternatively, the shaft is bent by ninety degrees so that the other end of the shaft acts as an integral lever arm. Preferably, the undercut in the shaft is diamond shaped such that it increases in width as it increases in depth and then decreases in width as it decreases in depth. The diamond shaped undercut reduces the likelihood that upon deformation the shaft will break and produce jagged edges and metal fragments.

20 Claims, 2 Drawing Sheets

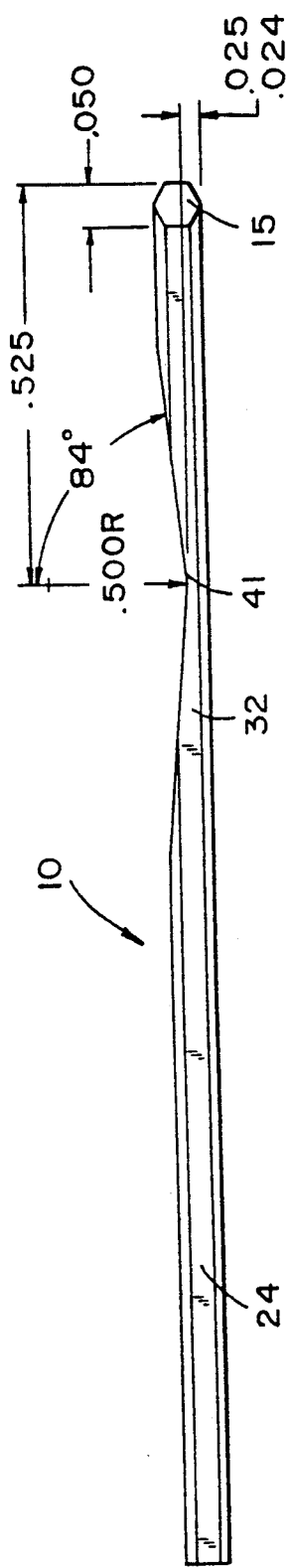
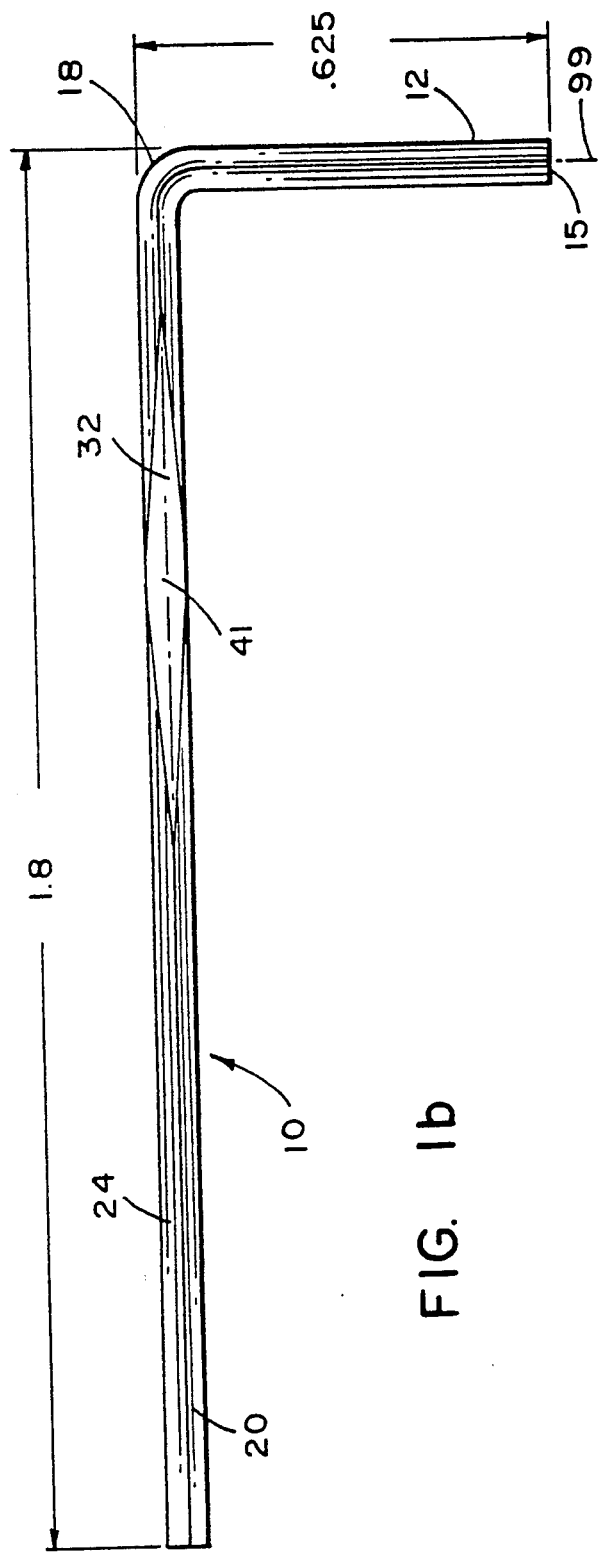
FIG. 1a
FIG. 1b

DISPOSABLE TORQUE WRENCH FOR DENTAL COMPONENTS

BACKGROUND OF THE INVENTION

1. Field of the Invention

The present invention relates to torque wrenches for dental components. More particularly, the invention relates which to a disposable torque wrench for applying a selected maximum torque during installation of a prosthetic component onto a dental implant.

2. State of the Art

Torque wrenches are known to be useful in medicine and dentistry. For example, U.S. Pat. No. 4,304,445 to Bailey et al. discloses a "Dental Wrench" having a structure which permits application of differing torques to the bur securing collet of a dental handpiece and the end cap of a turbine housing in a single wrench assembly. The Bailey et al. wrench has a shaft which engages the bur securing collet, and which is supported rotatively in a frame member and secured to a support member which has means for engaging the end cap of the turbine housing. Interlocking means are provided between the support member and the frame member so that the wrench can be rotated as a unitary assembly to secure or remove the end cap of a turbine housing. The interlocking means are releasable so that the shaft can be rotated independently within the frame member to secure or remove a dental bur in or from the collet of the handpiece housing. That portion of the frame member which is gripped for securing the end cap of the housing is of larger diameter relative to the support member so that increased torque can be applied to the end cap when the interlocking means is engaged to securely fasten the cap to the housing.

Another dental torque wrench with a similar purpose is disclosed in U.S. Pat. No. 3,935,761 to Junkel et al. The torque wrench of Junkel et al. includes a unitary angular C-shaped body, one of the arms of the body being provided with a socket, and a recess for accurately locating the wrench in position relative to the head of a handpiece when chuck adjustment (or removal) is desired. Between the paired arms is a knurled cylindrical wheel dimensioned to fit comfortably between, and be rotated by, the same fingers that receive the narrower connecting portion of the C-shaped body. A torsion spring shaft extends through the wheel and into the socket and has a non-circular end portion receivable with in opening of a handpiece chuck for locking the two parts (chuck and shaft) against independent relative rotation. A shoulder of the shaft limits the extent that the end portion may be inserted into the chuck opening, and the substantial length of that shaft, and its relationship with the other parts of the wrench, result in a torsional flexure of the shaft upon chuck tightening that signals the user when the torque limit is approached. The shaft is spring-loaded for limited axial movement.

In addition to torque wrenches designed for adjusting dental tools, there are known torque wrenches for applying torque to dental implants, posts and other components. For example, U.S. Pat. No. 4,480,997 (reissue 31948) to Deutsch et al. discloses a "Dental Post and Wrench Therefor and Method of Restoring Bulk to a Tooth Root Therewith". This known wrench is used to apply a predetermined torque to a dental post to thread it into the tooth root for crown restoration. The wrench is small and designed to be manipulated with thumb and index finger. It has a manually rotatable driving handle, the interior of which is hollowed to form a chamber. The lower end of the chamber terminates in a closure wall that has a centrally located opening through which a driven shaft extends outwardly from the handle. The driven shaft has an enlarged head, the undersurface of which provides a clutch or engaging surface that engages with the facing engaging surface of the closure wall. The engaging surfaces of the head and the closure wall function as clutch means to transmit the drive from the drive handle to the driven shaft.

The known torque wrenches for use in dentistry are relatively complex and expensive, difficult to calibrate, and require repeated sterilizations. They all require either a clutch means, a spring loading, or interacting parts movable relative to each other. For the purpose of applying a maximum torque to a dental component, however, the ideal wrench is compact, simply constructed, inexpensive, easy to use, and disposable. It should have few, if any, relatively moving parts.

SUMMARY OF THE INVENTION

It is an object of the present invention to provide a torque wrench particularly suited for use in applying a selected maximum torque to a dental component.

It is another object of the invention to provide a torque wrench which is simple to construct, easy to use and inexpensive enough to be disposable after one use.

A further object of the invention is to provide a torque wrench suitable for use with dental implant prosthetic components which permits a predetermined maximum torque to be applied to the component during restoration.

An additional object of the invention is to provide a dental component torque wrench which deforms so as to become unusable upon the application of a selected maximum torque, but which does not break.

The objects of the invention are achieved by a wrench constructed of a single integral piece of a metal which is preferably of hexagonal cross-sectional and of a desired thickness, and which has an undercut or valley portion at a desired location in its torque arm so that the torque arm of the wrench is deformed when a predetermined torque is applied through the torque wrench to a dental implant component. Preferred aspects of the invention include the use of a diamond shaped undercut in the wrench which increases in width as it increases in depth, and then decreases in width as it decreases in depth. The diamond shaped undercut is effective in causing the wrench to deform at the desired torque without breaking off and leaving jagged surfaces and metal particles in the mouth. A first preferred embodiment of the invention provides a torque wrench which is comprised of a single rod bent through a ninety degree turn so that it provides a torque arm with the diamond-shaped undercut, and a perpendicular drive shaft which mates with the dental implant or an attachment thereto. A second embodiment of the invention provides a torque wrench which is a straight rod with an undercut therein. The top end of the straight rod is adapted for insertion into a driving tool, while the bottom end mates with the dental implant component or an attachment thereto.

Additional objects and advantages of the invention will become apparent to those skilled in the art upon reference to the detailed description taken in conjunction with the provided figures.

BRIEF DESCRIPTION OF THE DRAWINGS

FIGS. 1a and 1b are respectively side and top views of a first embodiment of the torque wrench of the invention where the torque wrench has a ninety degree bend;

DETAILED DESCRIPTION OF THE PREFERRED EMBODIMENT

Figure 2:
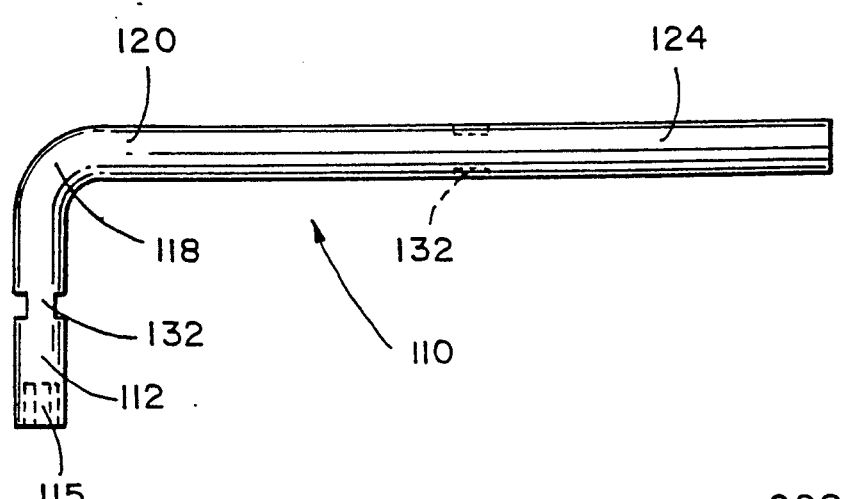
FIG. 2 is a diagram of a second embodiment of the ninety degree bend torque wrench of the invention.

Referring now to FIGS. 1a and 1b, a first preferred torque wrench 10 is shown. Torque wrench 10 is formed from a single integral shaft of annealed steel 20 (8650 alloy with Rockwell hardness of between C50 and C60) having a hexagonal cross-section (see FIG. 1a). In the embodiment of FIGS. 1a and 1b, the integral shaft 20 is provided with a bend 18 so that it forms a lever arm 24 and an engaging arm 12. Because the shaft 20 has a hexagonal cross-section, the end 15 of engaging arm 12 can engage hexagonally shaped socket. Thus, dental components (not shown) which are provided with such a hex shaped socket may be engaged by the end 15 of the engaging arm 12 so that when the lever arm 24 is moved around the axis 99 of engaging arm 12, a torque is applied to the engaged component.

It is an important feature of the invention that the wrench 10 be constructed of material so that it will deform when a predetermined force is applied to the shaft 20. There are many such known materials and it will be recognized that the dimensions of the arms 12 and 24, together with the properties known about the material from which it is constructed will determine at what force the shaft will deform. In this regard, it has been discovered that by providing relieved dimensions at one or more portions 32 of the shaft 20 ensures that the shaft 20 will deform reliably upon application of a predetermined force. In this manner, the torque wrench can be used to provide a torque of no more than a predetermined amount on a dental implant component which is being driven into the implant which in turn is secured in the mandibular or maxillary bone.

In the preferred embodiment of FIGS. 1a and 1b, one portion 32 of relieved dimension is shown in the lever arm 24 of shaft 20. As shown, the relieved dimension portion 32 is generally diamond shaped such that it increases in width (as seen in FIG. 1b) as it increases in depth (as seen in FIG. 1a), and then decreases in width as it decreases in depth. It has been found that by tapering the "undercut" in at least one and preferably two dimensions, when the torque wrench is deformed by application of force in excess of the maximum desired force, the wrench will not break. Thus, no jagged edges or metal pieces will be generated In the preferred embodiment of the invention, the shaft 20 is 0.050 inches in diameter (flat to flat) and approximately 2.4 inches long. When bent, the lever arm 24 itself is approximately 1.8 inches long, and the driving or engaging arm 12 is approximately 0.625 inches long. The relieved portion 32 is between 0.75 and 0.8 inches long and extends the entire width of the shaft 20 at the middle location 41 of the relief which is approximately 0.50 inches from the axis 99 of engaging arm 12. At the middle location 41 of the relief, the shaft 20 is undercut a full half-width such that the diameter at location 41 is approximately 0.025 inches. As shown, the relieved portion 32 is essentially symmetrical and angles downward and upward at an angle of approximately six degrees while it widens and narrows at an angle of approximately six degrees (about three degrees on either side of a middle axis). With 8650 alloy annealed steel and the provided dimensions, the lever arm 24 will deform when approximately 22 Newton-cm torque is applied through engaging arm 12 to a dental implant. In this manner, a known maximum torque force is applied to the dental implant component, thereby guaranteeing the desired force for installation while preventing excess force which could break the implant itself, the component, or the biological interface established between the implant and bone.

Those skilled in the art will appreciate that the torque wrench 10 with the bend 18 and relieved portion 32 may be manufactured either through casting and/or milling.

Referring now to FIG. 2, a second embodiment of a ninety degree bend torque wrench 110 is seen. Torque wrench 110 is comprised of a single cylindrical shaft 120 which has a bend 118 of ninety degrees and thereby forms arms 112 and 124. Torque wrench 110, is shown to be wider in cross section than torque wrench 10 of FIGS. 1a and 1b, and is provided at the end of arm 112 with a hexagonal indentation or countersunk area 115 which can mate with an external hexagonal protrusion such as a hex nut (not shown). Other differences between torque wrench 110 of FIG. 2 and torque wrench 10 of FIGS. 1a and 1bare the inclusion of shaped undercut or relief 132 in the driving/engaging arm 112 rather than the preferred tapered diamond shaped relief in the lever arm.

It will be appreciated that aspects of the torque wrench of FIG. 2 can be applied to the torque wrench of FIGS. 1a and 1b and vice versa. For example, the torque wrench of FIG. 2 could utilize a relief in arm 124 (as shown in phantom) instead of or in conjunction with the provided relief in arm 112. The use of two reliefs could be used as a safeguard to guarantee that the wrench will deform before an undesirable large torque is applied to the dental implant component. Likewise, borrowing from FIGS. 1a and 1b to FIG. 2, the relief section(s) 132 could be diamond shaped and tapering as shown in FIGS. 1a and 1b. On the other hand, torque wrench 10 could likewise be changed to apply the relief 32 in arm 12 instead of arm 24, and the shape and location of the relief could be changed as desired.

Figure 3:
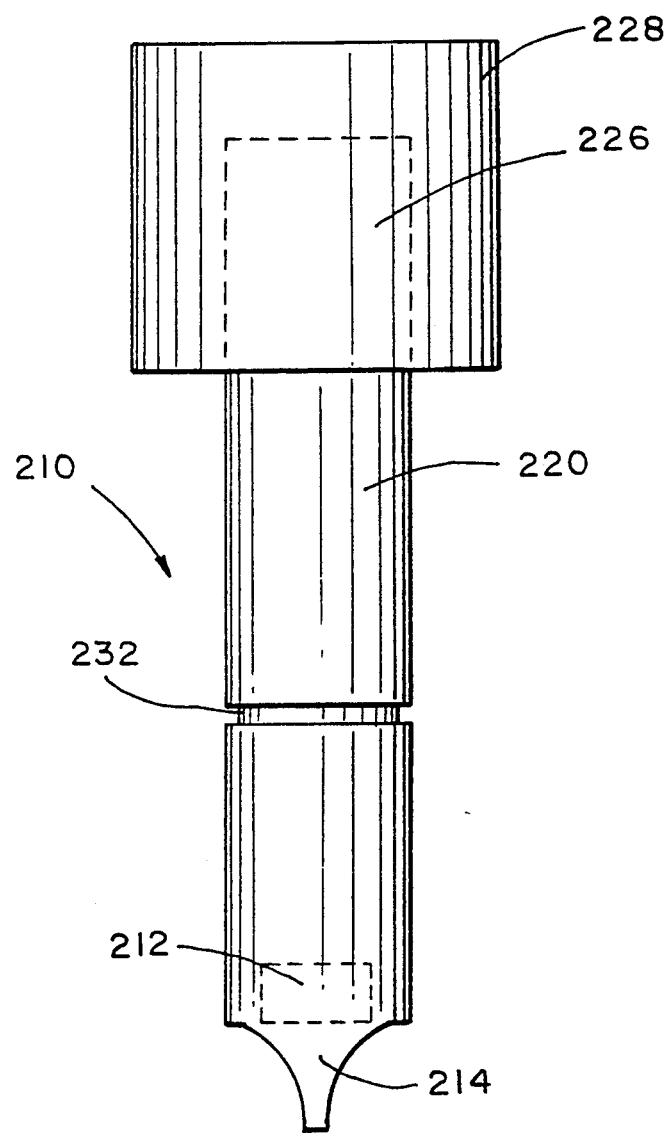
FIG. 3 is a cross-sectional view of a third embodiment of the torque wrench invention intended for use with a driving tool.

A third embodiment 210 of the wrench of the invention is shown in FIG. 3 where shaft 220 is an unbent single unitary shaft. Thus, torque wrench 210 is not provided with a lever arm (24 in FIG. 1), but rather, shaft 220 is adapted to have a second engaging end 226. The second engaging end 226 is designed to engage a driving means (e.g., handle or a motor drive) 228. The other end of shaft 220 is designed either with a hexagonal protrusion as indicated at 214, or alternatively with a hexagonally arranged receiving means or indentation 112 (shown in phantom). The torque wrench 210 of FIG. 3 is also provided with a portion of relieved dimension 232 which functions in the same or a similar way to the relief portions of the embodiments of FIGS. 1a, 1b, and 2. It should be appreciated that just as torque wrench 210 is provided with a second engaging end 226 for engaging a motor drive or the like 228, the lever arm of the torque wrenches 10 and 110 of FIGS. 1a, 1b, and 2 can be provided at the end of their lever arms with means for engaging a handle or other driving mechanism.

The advantages of the torque wrenches of the invention are that they are simple and extremely inexpensive to manufacture, easy to use, and very reliable. In addition, the torque wrenches with the tapered undercut are less likely to break and leave jagged edges and metal fragments. The wrenches are intended to provide a selected maximum torque to a dental implant component, at which point they deform and are discarded after one use.

There have been illustrated and described herein torque wrenches for dental implant components. While particular embodiments of the invention have been described, it is not intended that the invention be limited thereto, as it is intended that the invention be as broad in scope as the art will allow and that the specification be read likewise. Thus, while a particular steel alloy was described as the preferred material of the invention, it will be appreciated that other materials, or other alloys could be utilized. Likewise, while particular dimensions were described in the preferred embodiment, including the diameter of the steel, the distance from the relief to the curve in the steel, the depth of the relief, etc., it will be appreciated that other dimensions could be utilized with the exact same material to provide the same maximum torque. With other materials, clearly, other dimensions could be utilized. Also, if a different maximum torque were required, other dimensions, shapes, and/or materials could be utilized to obtain the same. It will therefore be appreciated by those skilled in the art that yet other modifications could be made to the provided invention without deviating from its spirit and scope as so claimed.

We claim:

1. A torque wrench for a dental implant component, comprising:
    a single integral shaft having a first end, a second end, and a middle portion having an undercut therein, said first end having a first engaging means for engaging said dental implant component, said first engaging means having one of an outer surface which is hexagonal in cross-section and an indentation which is hexagonal in cross-section, wherein said shaft is constructed of a preselected material and dimensioned to a first preselected cross-sectional thickness, and said undercut being located at a preselected location along said shaft and undercutting said shaft to at least one preselected cross-sectional thickness such that said shaft deforms substantially and noticeably without breaking at said undercut when a predetermined torque is applied through said shaft to said dental implant component.

2. A torque wrench according to claim 1, wherein: said middle portion of said shaft has a substantially ninety degree bend therein with a first portion of said shaft from said bend to said second end thereby acting as a lever arm.

3. A torque wrench according to claim 2, wherein: said undercut is located in said lever arm.

4. A torque wrench according to claim 3, wherein: said undercut is generally diamond shaped and increases in width as it increases in depth and then decreases in width as it decreases in depth.

5. A torque wrench according to claim 4, wherein: said single integral shaft is hexagonal in cross section.

6. A torque wrench according to claim 1, wherein: said single integral shaft is hexagonal in cross section.

7. A torque wrench according to claim 1, wherein: said undercut is generally diamond shaped and increases in width as it increases in depth and then decreases in width as it decreases in depth.

8. A torque wrench according to claim 5, wherein: said middle portion of said shaft has a substantially ninety degree bend therein with a first portion of said shaft from said bend to said second end acting as a lever arm, and with a second portion of said shaft from said bend to said first end acting as a driving arm.

9. A torque wrench according to claim 8, wherein: said preselected material is alloy 8650 annealed steel, said undercut is located in said lever arm, said first preselected cross-sectional thickness is approximately 0.050 inches in diameter, said lever arm is approximately 1.8 inches long, said driving arm is approximately 0.625 inches long, said undercut is approximately 0.775 inches long and said undercut starts at a first location and angles downward at approximately six degrees and widens at approximately six degrees as it angles downward to a middle location having said at least one second preselected cross-sectional thickness, and angles upward at approximately six degrees and widens at approximately six degrees as it angles upward to a second location, wherein said second preselected cross-sectional thickness is approximately 0.025 inches in diameter, and said middle location is approximately 0.5 inches from said bend, and said predetermined torque is approximately 22 Newton-cm.

10. A torque wrench according to claim 9, wherein: said single integral shaft and said outer surface of said first engaging means are hexagonal in cross-section.

11. A torque wrench according to claim 5, wherein: said outer surface of said first engaging means is hexagonal in cross-section.

12. A torque wrench according to claim 1, wherein: said first engaging means has an indentation which is hexagonal in cross-section.

13. A torque wrench according to claim 1, wherein: said second end has a second engaging means for engaging a drive means.

14. A torque wrench according to claim 1, wherein: said undercut increases in width as it increases in depth and then decreases in width as it decreases in depth.

15. A torque wrench according to claim 1, wherein: said undercut is generally diamond shaped.

16. A torque wrench for a dental implant component, comprising:
    a single integral shaft having a first end, a second end, and a middle portion having an undercut therein, said first end having a first engaging means for engaging coupling means coupled to said dental implant component upon which a torque is to be applied, wherein said shaft is constructed of a preselected material and dimensioned to a first preselected cross-sectional thickness, and said undercut being located at a preselected location along said shaft and undercutting said shaft to at least one preselected cross-sectional thickness such that said shaft deforms substantially and noticeably without breaking at said undercut when a predetermined torque is applied through said shaft to said dental implant component.

17. A torque wrench according to claim 16, wherein: said middle portion of said shaft has a substantially ninety degree bend therein with a first portion of said shaft from said bend to said second end thereby acting as a lever arm.

18. A torque wrench according to claim 16, wherein: said undercut increases in width as it increases in depth and then decreases in width as it decreases in depth.

19. A torque wrench for a dental implant component, comprising:

a single integral shaft having a first end, a second end, and a middle portion having an undercut therein, said first end having a first engaging means for engaging said dental implant component, said first engaging means having one of an outer surface which is hexagonal in cross-section and an indentation which is hexagonal in cross-section, wherein said shaft is constructed of a preselected material and dimensioned to a first preselected cross-sectional thickness, and said undercut being located at a preselected location along said shaft and undercutting said shaft to at least one preselected cross-sectional thickness such that said shaft deforms at said undercut when a predetermined torque is applied through said shaft to said dental implant component, said undercut increasing in width as it increases in depth and then decreasing in width as it decreases in depth.

20. A torque wrench according to claim 19, wherein: said undercut is generally diamond shaped.

* * * * *